United States Patent [19]
Belfer

[11] Patent Number: 6,092,523
[45] Date of Patent: Jul. 25, 2000

[54] ANTI-SNORING DEVICE

[76] Inventor: William A. Belfer, 804 W. Park Ave., Ocean, N.J. 07712

[21] Appl. No.: 09/427,330

[22] Filed: Oct. 26, 1999

[51] Int. Cl.[7] .......................................................... A61F 5/56
[52] U.S. Cl. ............................ 128/848; 128/859; 602/902
[58] Field of Search ..................................... 128/846, 848, 128/859–862; 602/902; 433/6

[56] References Cited

U.S. PATENT DOCUMENTS

| | | | |
|---|---|---|---|
| 3,692,025 | 9/1972 | Greenberg | 128/861 |
| 5,117,816 | 6/1992 | Shapiro | 128/848 |
| 5,720,302 | 2/1998 | Belfer | 128/848 |
| 5,810,013 | 9/1998 | Belfer | 128/848 |
| 5,921,241 | 7/1999 | Belfer | 128/848 |

*Primary Examiner*—Michael A. Brown
*Attorney, Agent, or Firm*—Robert M. Skolnik

[57] ABSTRACT

An anti-snoring device has a dental overlay portion and a guide ramp portion slidably mounted in the dental portion. The dental overlay is professionally fitted on a user's upper teeth. The guide ramp portion comfortably fits on the user's lower jaw to cause advancement of the lower jaw and tongue to thereby open the airway. The position of the ramp relative to the dental overly is locked in place with a sliding tabbed lock which fits into notches provided on an elongated stick secured to the guide ramp. The guide ramp permits lateral motion so that the lower jaw and TMJ have freedom of movement laterally so that they do not become sore and stiff.

20 Claims, 5 Drawing Sheets

ANTI-SNORING DEVICE

BACKGROUND OF THE INVENTION

1. Field of the Invention

The present invention relates to an anti-snoring device.

2. Description of the Related Art

This application discloses an anti-snoring device of the types generally described in my prior U.S. Pat. No. 5,921,241, issued Jul. 13, 1999; U.S. Pat. No. 5,810,013, issued Sep. 22,1998 and U.S. Pat. No. 5,720,302, issued Feb. 24, 1998.

As disclosed in my aforementioned patents (the disclosures of which are incorporated by reference herein), snoring or sleep apnea is caused by the condition where the tongue relaxes and contributed to blocking off the air passageway in the pharynx or lingual compartment. The soft tissue within the mouth cavity including the tongue, the pharyngeal folds, the soft palate, the muscalaris uvulae and the palatepharyngeal arch tend to vibrate as tidal air flows past during sleep which also causes snoring.

When the tongue musculature relaxes during sleep, gravity causes the tongue to drift inferiorly and posteriorly, thereby impacting or occluding against the surrounding structures of the airway, including the uvulvae and soft palate. When the airway is thus occluded, the patient gasps for air, a condition known as obstructive sleep apnea.

Anti-snoring devices are effective when they protract (pull or hold) the mandible (lower jaw) forward and upward and elevate the tongue, superiorly and anteriorly, so that the tongue does not occlude the air passageway by drifting inferiorly and posteriorly while sleeping. Most anti-snoring devices accomplish this task by holding the lower jaw forward against a rigid dental overlay component, which is fixed to the upper teeth, or to the upper and lower teeth. These anti-snoring devices fix the dental overlay component from falling out of the mouth by clasping or biting of the user's teeth into the dental overlay component and by close adaptation to the user's teeth.

There are two general classes of these oral appliances. One group, known as custom appliances, are formed as rigid plastic structures that are made by dental laboratories upon molds of a patient's teeth. Custom appliances are made of methacrylate resins. The other group, known as boil and bite appliances, is made from moldable thermolabile elastomeric materials such as ethylene vinyl acetate, and may also employ a hard plastic substructure. These devices need no dental impressions or lab procedures and are custom fitted directly upon the patient.

Boil and bite devices are first softened in near boiling water for between several seconds and one minute. The softened device is then placed on the upper or lower teeth. The patient is instructed to bite into the softened material to make an impression of the teeth in the softened material, allow the material to cool while it molds to the teeth. In some cases, excess material is then trimmed away. The appliance is then tested for comfort and fit.

Both classes of devices advance the lower jaw and the tongue (which is attached to the lower jaw) so that the tongue does not occlude the airway and normal respiration can take place. However, the devices differ in their ability to allow the lower jaw freedom of lateral motion.

The freedom to move the lower jaw laterally while it is held in its advanced posture is necessary to prevent soreness in the temporomandibular joints (TMJ) and the surrounding facial musculature. When the mandible is restricted from moving all night long the temporomandibular joints become stiff and the masticatory muscles and joints become temporarily dysfunctional. This results in the patient's non-compliance with the therapy.

Some of the rigid plastic anti-snoring devices (the custom appliances) permit lateral motion of the lower jaw. Such devices incorporate swivels or hinge mechanisms to join opposing upper and lower plates. In the boil and bite appliances, such hinges or swivels have been difficult to incorporate. In addition, such hinges and swivels require use of substantial interocclusal space. Interocclusal space is the vertical spacing between the opposing jaws when the jaws are in their normal resting posture (rather than closed together). If unduly thick or bulky anti-snoring appliances impinge upon this space, it is uncomfortable for the patient, it is more difficult to achieve required mandibular advancement, and the efficacy and patient compliance are decreased.

The prior art boil and bite appliances that permit lateral movement of the lower jaw while it is postured in the advanced position are disclosed in my aforementioned patents and in Halstrom U.S. Pat. No. 5,868,138. The Halstrom "boil and bite" appliance is a double plate structure joined by a swivel stem and hole assembly, which adjustably couples the upper and lower plates. It is bulky and thus it is difficult for the patient to close the lips over the appliance when it is placed in the mouth. The patient must open the mouth very wide to bite into the softened material. A clinician's assistance is required to properly place the appliance between the jaws and to properly align the teeth within the appliance. Patients cannot do this themselves with assured accuracy; thus, misalignment reduces the efficacy and adjustabililty of the appliance.

Double plate appliances require more space than signal plate appliances to accommodate the mechanical swivel, to provide sufficient space between the upper and lower plates to allow the patient sufficient tongue space, and to provide air holes for breathing.

The appliances disclosed in my aforementioned patents are single plate structures having no upper plate. They provide freedom of lateral motion, adequate tongue space, and sufficient space for passage of air during breathing.

Other boil and bite appliances of the prior art are single component structures, which utilize an upper dental plate and have a lower guide ramp, which engages the lower jaw just behind the lower teeth. The guide ramp in these devices is fixed to the upper dental plate so that the mandible is rigidly or nearly rigidly held in the anterior advancement. These appliances require skilled manipulation by a dentist. For example, the appliance disclosed in Shapiro, et al U.S. Pat. No. 5,117,816 uses a special handle to place the softened appliance properly and guide the mandible into its forward posture. Often, locating the correct jaw advancement to achieve reduction of obstructive sleep apnea is difficult. Often, the mandible is incorrectly advanced so that the patient closes down into the softened device incorrectly resulting in TMJ pain and decreased efficacy of the appliance.

The re-fitting process to locate correct jaw advancement requires that the appliance be re-softened and re-inserted in the mouth to imprint a more forward jaw posture into the material.

Another appliance disclosed in U.S. Pat. No. 5,092,346 to Hays and Meade manually places the appliance but requires periodic trimming and remolding of the ramp by softening the appliance in hot water to effect sequential mandibular advancement.

The prior art boil and bite guide ramp appliances do not provide sufficient lateral motion. Many of the prior art custom appliances that provide the required amount of lateral motion are either too costly, or too difficult for the non-dentist technologist to fit.

SUMMARY OF THE INVENTION

The present invention provides an anterior guide ramp which moves freely anteriorly, posteriorly and laterally from beneath the upper plate. The guide ramp is adjustable via a sticklike anterior extension, which passes through the body of the upper plate. This structure provides the needed degrees of lateral motion without use of a complete lower dental plate. The hole in the plate in which the stick slides is slightly larger than the dimensions of the stick to permit the guide ramp a range of lateral swing of approximately 15° from the right to the left.

The present invention is an anti-snoring device having an upper boil and bite dental overlay component, which attaches to the user's upper teeth, and an anteriorly adjustable lower ramp component attached to the upper dental overlay component. The ramp component is adjusted by the anterior movement of an adjusting shaft or stick (which may be horizontal, relative to the other components of the device) attached to the ramp component and passing through the front of the dental overlay component. Alternatively, the device may be made as a custom appliance with a laboratory made custom upper dental plate to which is added a preformed guide ramp from materials which are more durable than those used in the "boil and bite" embodiment. The shaft has a locking mechanism so that the dental overlay component remains in a constant position while the ramp component may be moved and secured in one of several available anterior positions relative to the position of the dental overlay component. When it is locked in place, the ramp is free to move laterally relative to the dental overlay.

In this manner, the ramp portion serves to hold the lower jaw in place and thereby inhibit posterior drift of the tongue during sleep in the supine position.

The present invention is easily fit without need for a jaw positioning handle or a positioning jig and without requiring special manipulative techniques to guide the patient's jaw into the ideal anterior posture. Thus, it may be easily fit by nondentists. The guide ramp is adjustable so that the patient can more easily and accurately bite into the softened material during initial fitting. Because the guide ramp can be moved rearwardly, the patient can bite onto the device without unduly straining the lower jaw by hyper-extending the jaw beyond the guide ramp.

The present invention permits the mandible to be advanced incrementally (i.e. titrated) by manual adjustment of the guide ramp. It eliminates the need for remolding to achieve sufficient sequential mandibular advancement to effect the required airway opening. There are no special tools required for advancing the jaw or for adjusting the anterior-posterior direction of the guide ramp. Refitting or re-positioning the mandibular advancement requires only a simple adjustment done with the device removed from the mouth, without the need for re-softening the appliance.

Alternatively, the mandible can be advanced while the device is being worn by gently pulling upon the extension stick handle. This method is utilized during sleep studies where the efficacy and usefulness of the device is tested.

A principal object and advantage of the invention is the provision of an anti-snoring device of the class described.

A further object and advantage of the invention is the provision of an appliance, which advances a patient's mandible and tongue.

Another object and advantage of the invention is the provision of an anti-snoring appliance having a sliding mechanism integrated into the body of the appliance to minimize the amount of vertical distance required between the jaws of a patient.

Still another object and advantage of the invention is an anti-snoring appliance, which provides sufficient space for a patient's tongue so that the tongue advancement is most effectively maximized when the mandible is advanced.

A still further object and advantage of the invention is the provision of an anti-snoring appliance which gives the patient good ability to breathe because the patient's tongue is not restricted in anterior advancement by bulky construction of the dental overlay.

A further object and advantage of the invention is the provision of an appliance which is not bulky and which is easily inserted in the mouth during molding.

Another object and advantage of the invention is the provision of an anti-snoring appliance which allows sufficient lateral motion of a patient's lower jaw movement at any amount of jaw advancement.

A further object and advantage of the invention is the provision of an anti-snoring appliance which is easy to bite into without need to hyper-extend a patient's mandible manually into the best advancement of the lower jaw.

A further object and advantage of the invention is the provision of an appliance which required no positioning jigs or incline ramp and/or handles to aid the patient in achieving correct jaw advancement.

Another object and advantage of the invention is the provision of an appliance, which requires no adjustment tools to titrate or calibrate the device.

Another object and advantage of the invention is the provision of an appliance which does not require remolding or refitting to achieve proper patient mandibular advancement.

A further object and advantage of the invention is the provision of an appliance which can be serially adjusted while it is being worn.

A further object and advantage of the invention is the provision of an anti-snoring appliance, which opens a patient's airway.

A still further object and advantage of the invention is the provision of an appliance which eliminates the need for costly dental laboratory procedures.

A further object and advantage of the invention is the provision of an appliance which may be used as a diagnostic tool.

A still further object and advantage of the invention is the provision of an appliance, which can be fit by persons without special training.

Another object and advantage of the invention is the provision of an appliance, which promotes proper alignment of the patient's tongue against the roof of the mouth.

A further object and advantage of the invention is the provision of an appliance, which provides a number of incremental settings.

A further object and advantage of the invention is the provision of an appliance, which may be used by patients with fewer than ten lower teeth without loss of retention.

A further object and advantage of the invention is the provision of an appliance which can be fabricated in one size for all patients.

Another object and advantage of the invention is the provision of an anti-snoring device, which provides breathing holes for oral respiration.

A still further object of the invention is the provision of an anti-snoring device having a dental overlay component and a ramp component, which allows lateral motion of the ramp relative to the position of the dental overlay component.

A still further object of the invention is to reverse the backward and downward movement of the tongue by advancing the lower jaw and the tongue to restore proper posture of the tongue and permit the unobstructed passage of inspiratory and expiratory air.

A still further object and advantage of the invention is the use of a template to aid in the softening and molding of the appliance in a small vessel of hot water.

A further object and advantage of the invention is the provision of an appliance where the upper dental overly has a preformed shape and form which can be molded to a patient without trimming or grinding to simplify fitting.

The foregoing, as well as further objects and advantages of the invention will become apparent to those skilled in the art from a review of the following detailed description of my invention, reference being made to the accompanying drawings.

DETAILED DESCRIPTION OF THE PREFERRED EMBODIMENT

Figure 1:
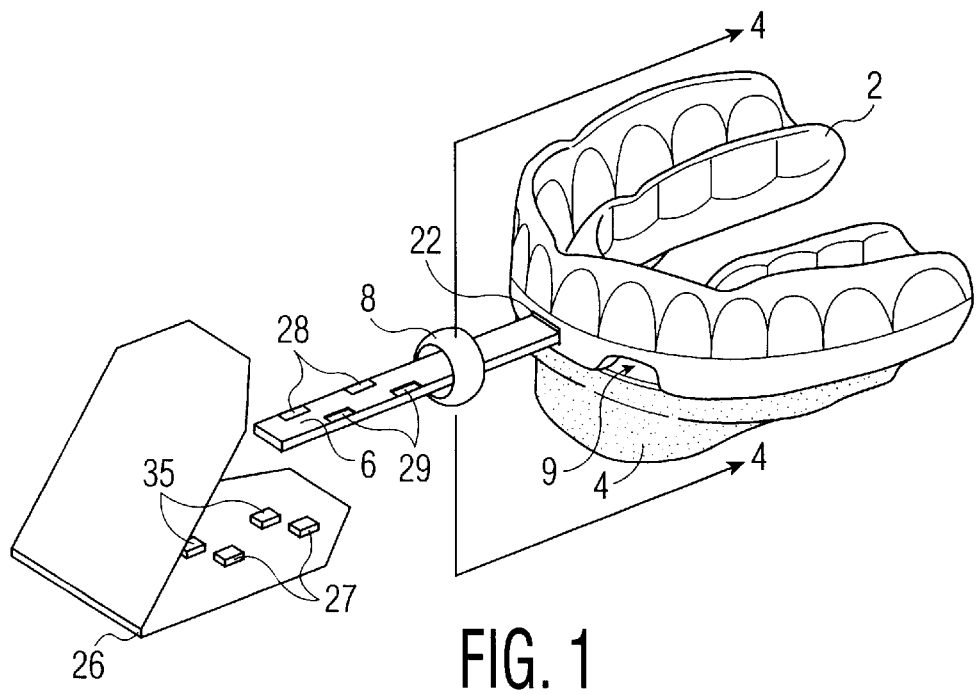
FIG. 1 is an exploded perspective view of my invention.

As shown in FIGS. 1–4, where like reference numerals are used to designate like parts, the anti-snoring device of the present invention includes a dental overlay portion or plate 2 and a guide ramp portion 4. The ramp portion 4 is connected to a horizontally moveable elongated stick 6. The stick 6 is slidably mounted in an aperture 22 in the front of the dental overlay portion 2. A lock 8 is slidably mounted on the stick 6. The aperture 22 in the plate 2 in which the stick slides is slightly larger than the dimensions of the stick to permit the guide ramp 4 a range of lateral swing of approximately 15°.

Breathing holes 9 (one of which is shown in FIG. 1) may be formed in the dental overlay portion 2 on opposite sides of the stick 6. These holes provide air passage through the appliance to aid in breathing though the mouth.

Figure 2:
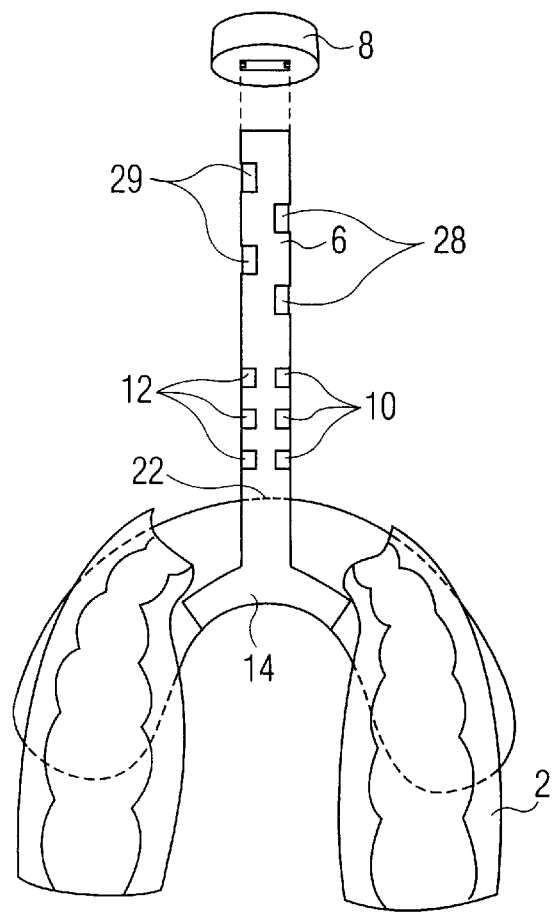
FIG. 2 is a top partially cut-away view of the device shown in FIG. 1.
Figure 3:
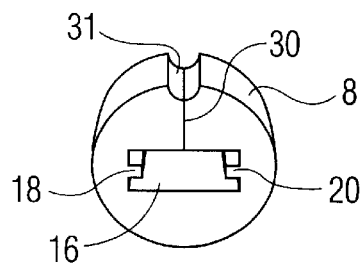
FIG. 3 is a perspective view of a portion of the device shown in FIG. 1.
Figure 4:
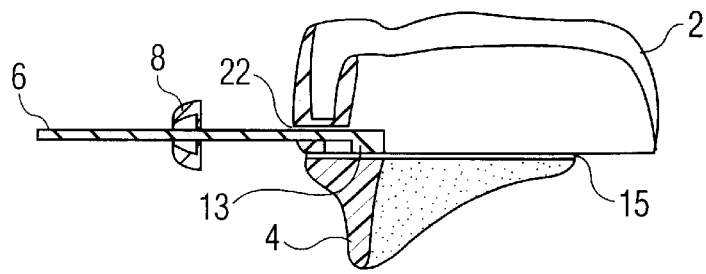
FIG. 4 is sectional view of the device of FIG. 1, taken along the line 4—4 of FIG. 1.

As more clearly shown in FIG. 2, the stick 6 has opposite pairs of notches 10 and 12 on the sides of the stick. These notches cooperate with flexible tab portions 18 and 20 (FIG. 3) which extend in to a central through aperture 16 in the slidable lock 8 to secure the lock in place and thereby, the position of the ramp portion 4 relative to the dental overlay portion 2. A slit 30 is cut into the lock 8. The lock 8 is notched at 31 at the top of the slit. The lock 8 can be "opened" by the use of a person's fingernail to separate the halves of the lock 8 along the silt 30. The lock 8 is formed of materials of sufficient flexibility for such use.

A removable handle 26 is provided with internal protrusions 27 and 35. The stick 6 has additional offset notches 28 and 29 formed near the front of the stick. The notches 28, 29, receive the protrusions 27 and 35 so that one can securely hold the appliance by the use of the handle 26. The handle also provides a means of holding the heated device without distorting it, while inserting it into the patient's mouth.

Figure 5:
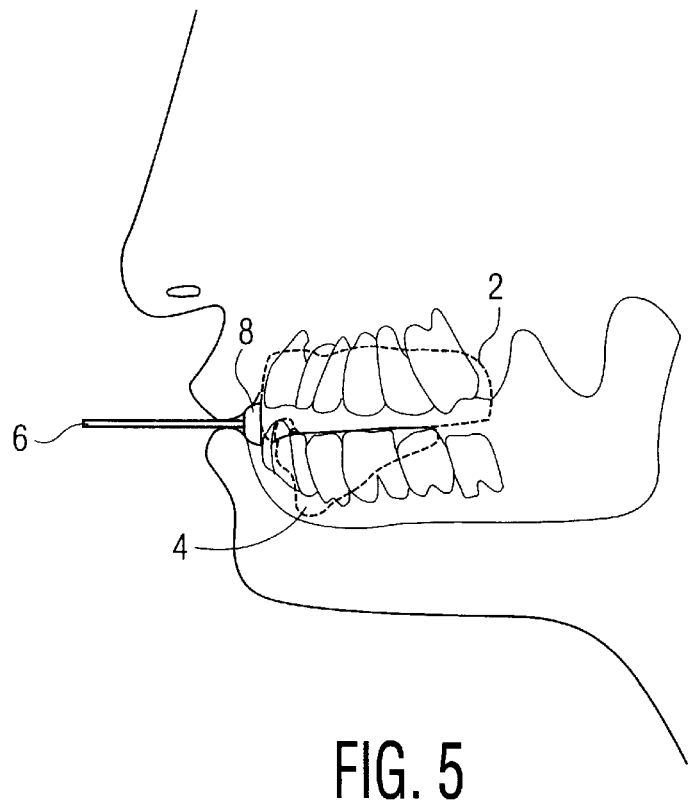
FIG. 5 is a side view of the device of FIG. 1 in use.

As shown in FIG. 5, the device of FIGS. 1–4 is inserted in the mouth. The dental overlay portion 2 serves to support the device in the mouth. A dentist fits the dental overlay portion 2 to the user. The appliance is titrated using the notches 10 and 12. The notches are spaced in 1.5-mm increments so that rearward movement of the slidable lock 8 advances the guide ramp 4 anteriorly relative to the dental overlay 2. By moving the lock incrementally, the therapist has control over the advancement so that the most advanced yet most comfortable jaw position can be determined.

Figure 6:
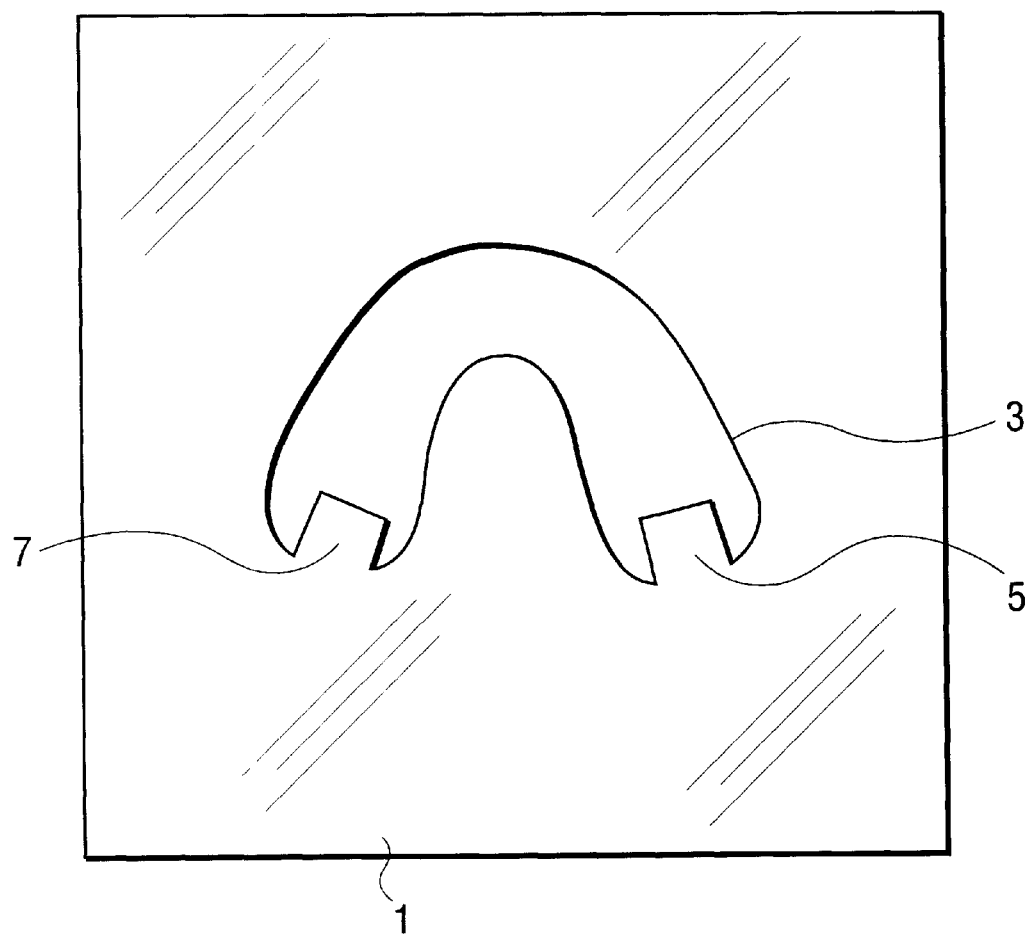
FIG. 6 is a plan view of a template used with the device of FIG. 1.

FIG. 6 shows a template, which is used as in the storage and heat (hot water) softening of the device of FIGS. 1–5. It is used in a two-stage process to warm both sides of the appliance, independently. The template 1 is a plastic plate having an aperture 3 therein, which is dimensioned to receive and support the dental overlay portion 2 therein. Tabs 5 and 7 are provided to secure the dental overlay portion 2 in the aperture. When supported in this manner, the device can be first softened in near-boiling water by covering only the overlay portion in a vessel of hot water. Then, the device is flipped over and the ramp is suspended in the hot water. The device can also be safely stored with decreased risk of damage.

Figure 7:
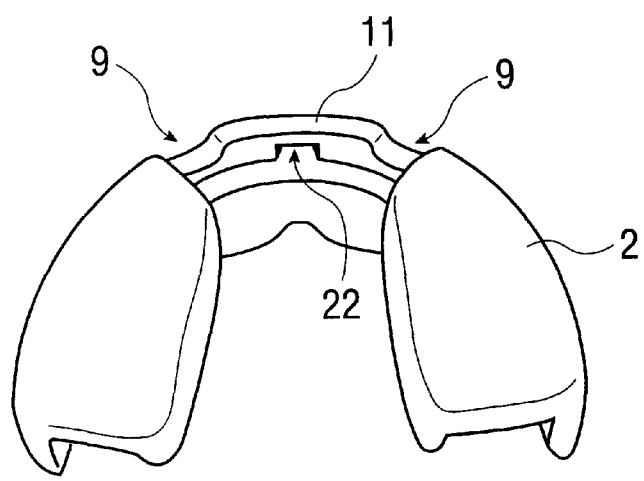
FIG. 7 is a rear perspective cut-a-way view of the dental overlay portion of the device of FIG. 1.

As shown in more detail in FIG. 7, the dental overlay portion 2 has two breathing holes 9 formed integrally in the front of the overlay. The breathing holes 9 are in either side of a curved supporting surface 11 also formed integrally in the front of the overlay.

Figure 8:
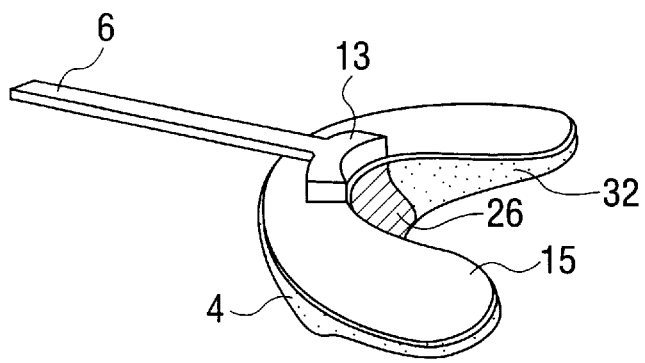
FIG. 8 is a perspective view of the guide ramp portion of the device of FIG. 1.
Figure 9:
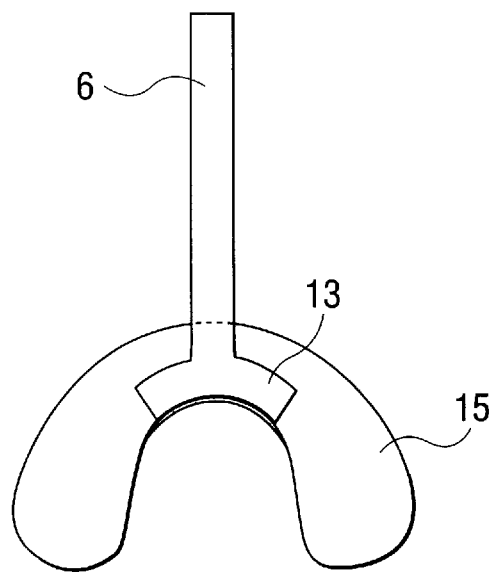
FIG. 9 is a top view of the guide ramp shown in FIG. 8.
Figure 10:
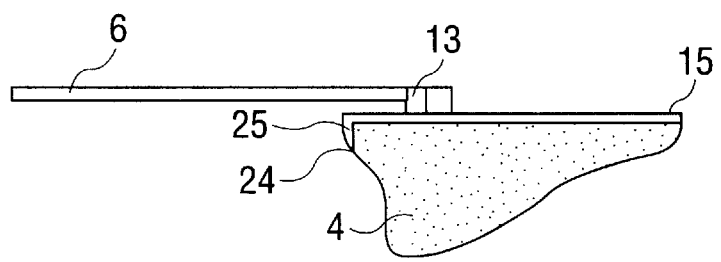
FIG. 10 is a side view of the guide ramp shown in FIG. 8.

FIGS. 8–10 show the guide ramp 4 of the appliance described in FIGS. 1–5. The guide ramp 4 has stick 6 attached to a curved ledge 13 formed on the base layer 15 of the guide ramp. A second material 32 is affixed to the base layer. The second material 32 may be softened by hot water. The base layer 15 is non-softening in hot water. The second material is shaped so that its front portion 24 may be supported against the interior of a patient's lower teeth. The rear portion of the second material 32 has a backing portion 26 of the same material as base layer 15. It is formed generally vertically. As shown in FIG. 10, a portion of base layer 15 is formed into an anterior lip 24 at the front of the second material 32.

Figure 11:
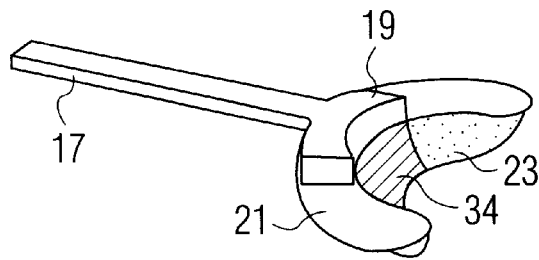
FIG. 11 is perspective view of another guide ramp useable in the device of FIG. 1.
Figure 12:
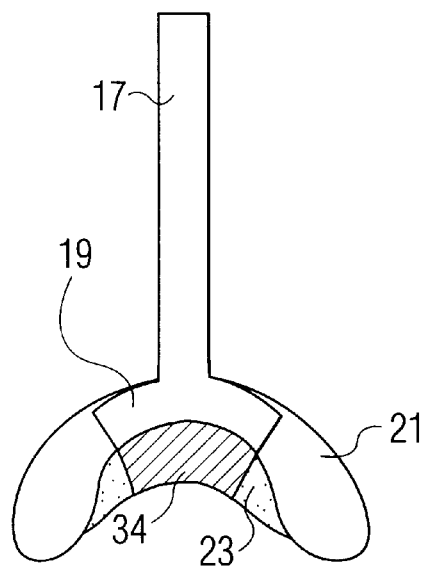
FIG. 12 is a top view of the guide ramp of FIG. 11.
Figure 13:
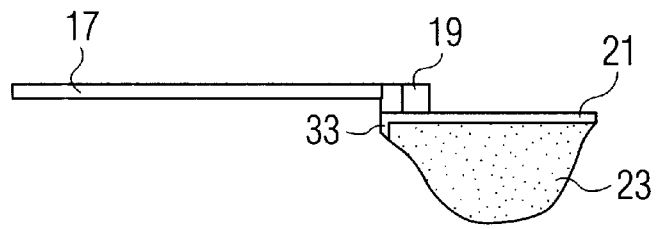
FIG. 13 is a side view of the guide ramp of FIG. 12.

FIGS. 11–13 shown another embodiment of a guide ramp useable with the appliance of FIGS. 1–5. In the embodiment of FIGS. 11–13, a stick 17 is attached to a curved supporting ledge 19. The ledge 19 is formed on a base layer 21 in the same manner as discussed in connection with elements 6, 13, and 16 of FIGS. 8–10; however, the shape of the softer material 23 and the location of the softer material 23 on the base layer 21 differ. Softer material 23 is affixed to base layer 21 such that a substantial area of the base layer forms a lip 25 above the front portion of the material 23. The rear portion of the material 23 forms a surface at an angle of approximately 45° at backing portion 34 and is smaller than the corresponding portion of the guide ramp of FIGS. 8–10. An anterior lip 33 is formed at the front of the soft material 23.

As will now be apparent, the curved supporting surface 11 shown in FIG. 7 mates with the corresponding curved ledges 13 and 19 of the guide ramps to support the guide ramp when it is in its advanced anterior position.

In both embodiments of the guide ramp, the soft material surface of the ramp, which contacts the incisor teeth, is convexly curved. The convex curvature approximates the anterior circumference of the dental arch. The rearward surface of the guide ramp is bi-concave and it encourages the user to posture his or her tongue against the roof of the mouth instead of below it, in the floor of the mouth. Hence, the anterior reposturing of the jaw has a maximum effect on reposturing the tongue.

In use, a trial fitting is done before the appliance is heated and molded. The guide ramp is positioned rearwardly (further away from the lower incisor teeth) so that the lower incisor teeth do not bite upon it when the appliance is trial fitted in the mouth. The dental overly is fitted upon the template so that all surfaces of the dental overlay (the upper plate) except the biting surface are is exposed to near boiling water for approximately 30 seconds. The template carrying the appliance is placed upon a mug or jar which is filled to its rim with the hot water. Holding the overlay by the stick extension, the appliance is then lifted off the template and the overlay placed over the upper teeth, and the patient bites down firmly. Then, the dentist or a therapist molds the outermost surface of the overlay with finger pressure. The existing concavities and tooth forms which are pre-molded into the appliance serve to grip the contours of the teeth during the molding process so that the appliance becomes self-retentive when it cools. The appliance is then allowed to cool in the mouth for approximately one minute. It is then soaked in cold water for an additional minute. The appliance is then re-placed onto the template with the guide ramp facing inferiorly into the water and it is heated for approximately 30 seconds. While holding the heated appliance by the flat end tab, the appliance is then placed in the patient's mouth. Then, the patient is instructed to advance the lower jaw and simultaneously, bite upon the incisor teeth in an edge to edge position. Concomitantly, the therapist pulls on the end tab of the stick so that the softened material becomes formed to the lingual (tongue side) surface of the incisor teeth. The device is permitted to cool once again. The guide ramp position is set in place by pushing the locking ring backward against the front of the dental overly. The extension stick is cut off, flush to the ring.

The upper dental plate and the moldable portion of the guide ramp may be formed of ethylene vinyl acetate (ELVAX®, offered by DuPont Co.). This material has a vinyl acetate contact of 33%, by weight, a VICAT softening temperature of 97° F., and a durometer of 73 shoreA. When the appliance is placed in hot water, it thus softens and takes on the impression of the teeth. The guide ramp is formed of a hard plastic understructure layer 15 or 21 as in FIGS. 8 and 11 upon which a layer of ELVAX® is applied. The guide ramp 4 is formed of two portions; a portion which is moldable and makes and impression of the lower anterior and/or posterior teeth; and a hard plastic base. The ELVAX portion is closely applied to the plastic base via inherent chemical adhesiveness of the ELVAX to plastic, or by mechanical locking means. The stick may be formed of the same material as the understructure of the guide ramp. Suitable materials are carboxylate resin, polypropylene, or other plastic that will remain hard and not distort in boiling water.

Further modifications to the apparatus of the invention may be made without departing from the spirit and scope of the invention; accordingly, what is sought to be protected is set forth in the appended claims.

What is claimed is:

1. An anti-snoring device comprising, a dental overlay having an aperture therein; a ramp having an elongated adjusting member attached thereto; said elongated adjusting member being slidably mounted in said aperture for anteriorly changing the relative positions of said dental overlay and said ramp; and locking means attached to said adjusting member for securing the position of said ramp.

2. The anti-snoring device of claim 1 wherein said aperture is larger than said elongated adjusting member for permitting said ramp to move in a range of lateral swing of approximately 15°.

3. The anti-snoring device of claim 1 further including flat tab handle means removably attached to said elongated adjusting member to facilitate holding the device.

4. The anti-snoring device of claim 1 wherein a patient's airway is open by anterior re-posturing of a patient's mandible and tongue.

5. The anti-snoring device of claim 1 wherein said dental overlay has a predetermined form for fitting onto a patient's teeth.

6. An anti-snoring device comprising, a dental overlay having an aperture therein; a guide ramp having an elongated adjusting member attached thereto; said elongated adjusting member being slidably mounted in said aperture for enabling lateral movement of said guide ramp relative to said dental overlay.

7. The anti-snoring device of claim 6 wherein said dental overlay covers the upper teeth of a user.

8. The anti-snoring device of claim 7 wherein said dental overlay component has breathing passages formed therein.

9. The anti-snoring device of claim 6 wherein said ramp promotes proper positioning of the user's tongue against the roof of the mouth.

10. The anti-snoring device of claim 7 wherein said elongated adjusting member has a plurality of notches formed therein.

11. The anti-snoring device of claim 10 wherein said locking means includes apertured means slidably mounted on said adjusting member for adjustably contacting said notches.

12. The anti-snoring device of claim 11 further including tab means formed in the aperture of said apertured means for engaging said notches.

13. The anti-snoring device of claim 6 wherein said dental overlay includes tooth shaped indentations formed therein for mechanically engaging a patient's teeth.

14. The anti-snoring device of claim 6 wherein adjustment and anterior fixation of said guide ramp does not inhibit lateral movement of said guide ramp.

15. The anti-snoring device of claim 6 wherein anterior movement of said guide ramp causes anterior re-posturing of a patient's mandible and tongue.

16. The anti-snoring device of claim of 15 wherein re-posturing of said guide ramp man be made outside the patient's mouth.

17. The anti-snoring device of claim 15 wherein re-posturing of said guide ramp may be made while the device is worn.

18. The anti-snoring device of claim 6 wherein lateral movement of said guide ramp permits lateral movement of a patient's jaw.

19. The anti-snoring device of claim 6 wherein lateral movement of said guide ramp allows lateral motion of the patient's mandible concomitantly with anterior re-posturing of the mandible.

20. A template for heating a boil and bite anti-snoring device comprising; a base, an aperture formed in said base, said aperture having a shape corresponding to the shape of a boil and bite anti-snoring appliance; tab means attached to said base and extending into said aperture for supporting a boil and bite anti-snoring appliance.

* * * * *